US00PP28741P3

(12) United States Plant Patent
Hammett

(10) Patent No.: US PP28,741 P3
(45) Date of Patent: Dec. 5, 2017

(54) ***DAHLIA* PLANT NAMED 'MYSTIC SPARKLER'**

(50) Latin Name: *Dahlia variabilis*
Varietal Denomination: Mystic Sparkler

(71) Applicant: Keith Hammett, Auckland (NZ)

(72) Inventor: Keith Hammett, Auckland (NZ)

( * ) Notice: Subject to any disclaimer, the term of this patent is extended or adjusted under 35 U.S.C. 154(b) by 125 days.

(21) Appl. No.: 14/756,775

(22) Filed: Oct. 10, 2015

(65) Prior Publication Data

US 2016/0113179 P1 Apr. 21, 2016

(30) Foreign Application Priority Data

Oct. 15, 2014 (AU) ..... PBR 2014/241

(51) Int. Cl.
*A01H 5/02* (2006.01)

(52) U.S. Cl.
USPC ..... Plt./321

(58) Field of Classification Search
USPC ..... Plt./263.1, 321
See application file for complete search history.

(56) References Cited

PUBLICATIONS

PLUTO: Plant variety Database, Apr. 12, 2017, US citation for 'Sparkler.' 1 page.*
PLUTO: Plant variety Database, Apr. 12, 2017, NZ citation for 'Mystic Sparkler.' 1 page.*
PLUTO: Plant variety Database, Apr. 12, 2017, AU citation for 'Mystic Sparkler.' 1 page.*
Easy to Grow Flower Bulbs website; page for *Dahlia* Sparkler. https://www.easytogrowbulbs.com/products/dahlia-sparkler?variant=31581284812. Accessed Apr. 12, 2017. 3 pages.*

* cited by examiner

*Primary Examiner* — Susan McCormick Ewoldt
*Assistant Examiner* — Karen Redden

(57) ABSTRACT

A new cultivar of *Dahlia* plant named 'Mystic Sparkler' that is characterized by an upright and uniform growth habit, grey-green compound leaves, red ray florets streaked with yellow and a yellow base and yellow disc florets.

1 Drawing Sheet

Botanical classification: *Dahlia variabilis.*
Variety denomination: 'Mystic Sparkler'.

BACKGROUND OF THE INVENTION

The present invention relates to a new and distinct cultivar of *Dahlia* plant botanically known as *Dahlia variabilis* and hereinafter referred to by the cultivar name 'Mystic Sparkler'.

The new cultivar is the product of a breeding program conducted by the inventor in a cultivated area of Auckland, New Zealand. The objective of the breeding program is to develop new *Dahlia* cultivars with interesting and unique flower colors.

'Mystic Sparkler' originated from the open pollination of the female or seed parent *Dahlia* 'Mystic Enchantment' (U.S. Plant Pat. No. 23,332). The male or pollen parent is unknown. The resulting seeds were subsequently planted and grown. The cultivar 'Mystic Sparkler' was selected in 2009 as a single plant within the stated progeny in a controlled environment of Auckland, New Zealand.

Asexual reproduction by terminal cuttings of the new cultivar 'Mystic Sparkler' was first performed in 2009 in Auckland, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Dahlia* cultivar 'Mystic Sparkler'. These traits in combination distinguish 'Mystic Sparkler' as a new and distinct cultivar apart from all other existing varieties of *Dahlia* known to the inventor.

1. *Dahlia* 'Mystic Sparkler' exhibits an upright and uniform growth habit.
2. *Dahlia* 'Mystic Sparkler' exhibits grey-green compound leaves.
3. *Dahlia* 'Mystic Sparkler' exhibits red ray florets streaked with yellow and a yellow base.
3. *Dahlia* 'Mystic Sparkler' exhibits yellow disc florets.

The closest comparison varieties are the female or seed parent plant *Dahlia* 'Mystic Enchantment' and *Dahlia* 'HS Flame' (U.S. Plant Pat. No. 18,426). 'Mystic Sparkler' is different than 'Mystic Enchantment' in having a smaller overall size and red ray florets streaked with yellow and a yellow base. The ray florets of 'Mystic Enchantment' are all red. 'Mystic Sparkler' is different than 'HS Flame' in having a smaller overall width and grey-green leaves. In contrast, the leaves of 'HS Flame' are brown.

BRIEF DESCRIPTION OF THE DRAWING

The accompanying photograph illustrates the distinguishing traits of *Dahlia* 'Mystic Sparkler'. The plant in the photograph shows an overall view of a 20 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Dahlia* cultivar named 'Mystic Sparkler'. Data was collected in Auckland, New Zealand from 20 week old outdoor grown plants in 12 cm. diameter containers. The time of year was June and the temperature averaged 17° Centigrade during the day and 10° Centigrade at night. The light level was natural outdoor light. Color determinations are in accordance with The Royal Horticultural Society Colour Chart 2001 edition, except where general color terms of ordinary dictionary significance are used. The growing requirements are similar to the species.

'Mystic Sparkler' has not been tested under all possible conditions and phenotypic differences may be observed with variations in environmental, climatic, and cultural conditions, however, without any variance in genotype.

Botanical classification: *Dahlia* 'Mystic Sparkler'.

Use: Ornamental.

Parentage: 'Mystic Sparkler' originated from the open pollination of the female or seed parent *Dahlia* 'Mystic Enchantment'.

Vigor: Moderate.

Growth habit: Broad upright.

Plant shape: Inverted triangle with flowers on top.

Suitable container size: 12 cm. container.

Height: 76 cm. in height.

Width: 21 cm. in width.

Hardiness: USDA Zone 8.

Propagation: Terminal cuttings.

Time to initiate roots: Approximately 12 days to produce roots on an initial cutting.

Time to produce a rooted cutting or liner: Approximately 28 days.

Crop time: From a rooted cutting, approximately 18 to 20 weeks are required to produce a finished flowering plant.

Root system: Fine and fibrous with stolons and tubers.

Stem:

*Branching habit.*—Free branching.
*Average number of lateral branches.*—8.
*Pinching.*—Yes.
*Lateral branch diameter.*—7 mm. in diameter.
*Lateral branch length.*—51 cm. in length.
*Lateral branch strength.*—High.
*Stem color.*—N186B.
*Pubescence.*—Absent.
*Internode length.*—3 cm. between nodes.
*Shape.*—Round.
*Surface.*—Smooth, slightly glossy.

Foliage:

*Texture.*—Slightly glossy.
*Leaf arrangement.*—Opposite.
*Compound or single.*—Compound.
*Quantity of leaves per lateral branch.*—6.
*Quantity of leaflets per leaf.*—3.
*Leaf length.*—12.5 cm. in length.
*Leaf width.*—10.4 cm. in width.
*Leaflet length.*—3.2 cm. in length.
*Leaflet width.*—2.8 cm. in width.
*Leaf shape.*—Hastate.
*Leaf apex.*—Apiculate.
*Leaf base.*—Attenuate.
*Pubescence.*—Absent.
*Leaf margin.*—Ciliate and pinnatisect.
*Vein pattern.*—Pinnate.
*Young leaf color (lower surface).*—187B.
*Young leaf color (upper surface).*—N189B.
*Mature leaf color (lower surface).*—187A.
*Mature leaf color (upper surface).*—N189A.
*Vein color (lower surface).*—187A.
*Vein color (upper surface).*—N189B.
*Leaf attachment.*—Petiolate.
*Petiole dimensions.*—1.4 cm. in length and 3 mm. in width.
*Petiole color.*—187A.

Inflorescence:

*Inflorescence type.*—Terminal, single row of ray florets surrounding a central cluster of disk florets.
*Inflorescence aspect.*—Upward and outward.
*Quantity of flowers per lateral stem.*—1.
*Quantity of flowers and buds per plant.*—Approximately 20.
*Flowering season.*—Summer and fall.
*Fragrance.*—Faint, sweet.
*Flower bud length.*—8 mm. in length.
*Flower bud diameter.*—10 mm. in diameter.
*Flower bud shape.*—Oblate.
*Bud color.*—152C.
*Flower aspect.*—Outward-upright.
*Flower dimensions.*—8.3 cm. in diameter, and 1.9 cm. in height.
*Flower longevity.*—Approximately 12 days.
*Ray floret number.*—10 to 12 per flower.
*Ray floret appearance.*—Dull.
*Ray floret texture.*—Smooth.
*Ray floret fused or unfused.*—Unfused.
*Ray floret shape.*—Obovate.
*Ray floret margin.*—Entire.
*Ray floret apex.*—Obtuse with acute tip.
*Ray floret base.*—Cuneate.
*Ray floret dimensions.*—3.6 cm. in length, 2.1 cm. in width.
*Ray floret color when opening (upper side).*—67B with streaks of 10B, base 10B.
*Ray floret color when opening (under side).*—67B.
*Ray floret color fully open (upper side).*—67B with streaks of 10B, base 10B.
*Ray floret color fully open (under side).*—67B.
*Ray floret color fading.*—164B.
*Disc floret number.*—40 to 50 per flower.
*Disc floret texture.*—Smooth.
*Disc floret shape.*—Tubular, corolla fused.
*Disc floret apex.*—Acute.
*Disc floret dimensions.*—1.0 cm. in length, 1.1 cm. in width.
*Disc floret color (upper side).*—14B.
*Disc floret color (under side).*—14B.
*Receptacle dimensions.*—6 mm. in depth and 2.1 cm. in diameter.
*Receptacle surface.*—Smooth.
*Receptacle color.*—200B.
*Self-cleaning or persistent.*—Self-cleaning.

Peduncle:

*Peduncle dimensions.*—16 cm. in length and 4 mm. in diameter.
*Peduncle angle.*—0°.
*Peduncle color.*—186B.
*Peduncle strength.*—Strong.

Reproduction organs:

*Stamen number.*—5 in number on disc florets only.

*Stamen length.*—6 mm.
*Anther shape*.—Connate.
*Anther dimensions.*—3 mm. in length.
*Anther color.*—25A.
*Amount of pollen*.—High.
*Pollen color.*—24A.
*Pistil number*.—One, on both ray and disc florets.
*Pistil length.*—10 mm.
*Stigma dimensions.*—3 mm. in. length and 0.4 mm. in width.
*Stigma form*.—Plumose.
*Stigma color.*—25A.
*Stigma shape*.—Bifurcate.
*Ovary position*.—Inferior.
*Ovary color*.—N144A.
*Ovary shape*.—Rotund.
*Ovary dimensions.*—2 mm. in width and 3 mm. in height.

Fruit and seed:
*Fruit shape*.—Napiform capsule.
*Fruit dimensions.*—27 mm. in length and 20 mm. in width.
*Fruit color.*—187A.
*Seed dimensions.*—10 mm. in length and 3.5 mm. in width.
*Seed color.*—187A.

Disease resistance: Plants of the new *dahlia* have not been observed for disease resistance.

The invention claimed is:

1. A new and distinct variety of *Dahlia* plant named 'Mystic Sparkler' as described and illustrated.

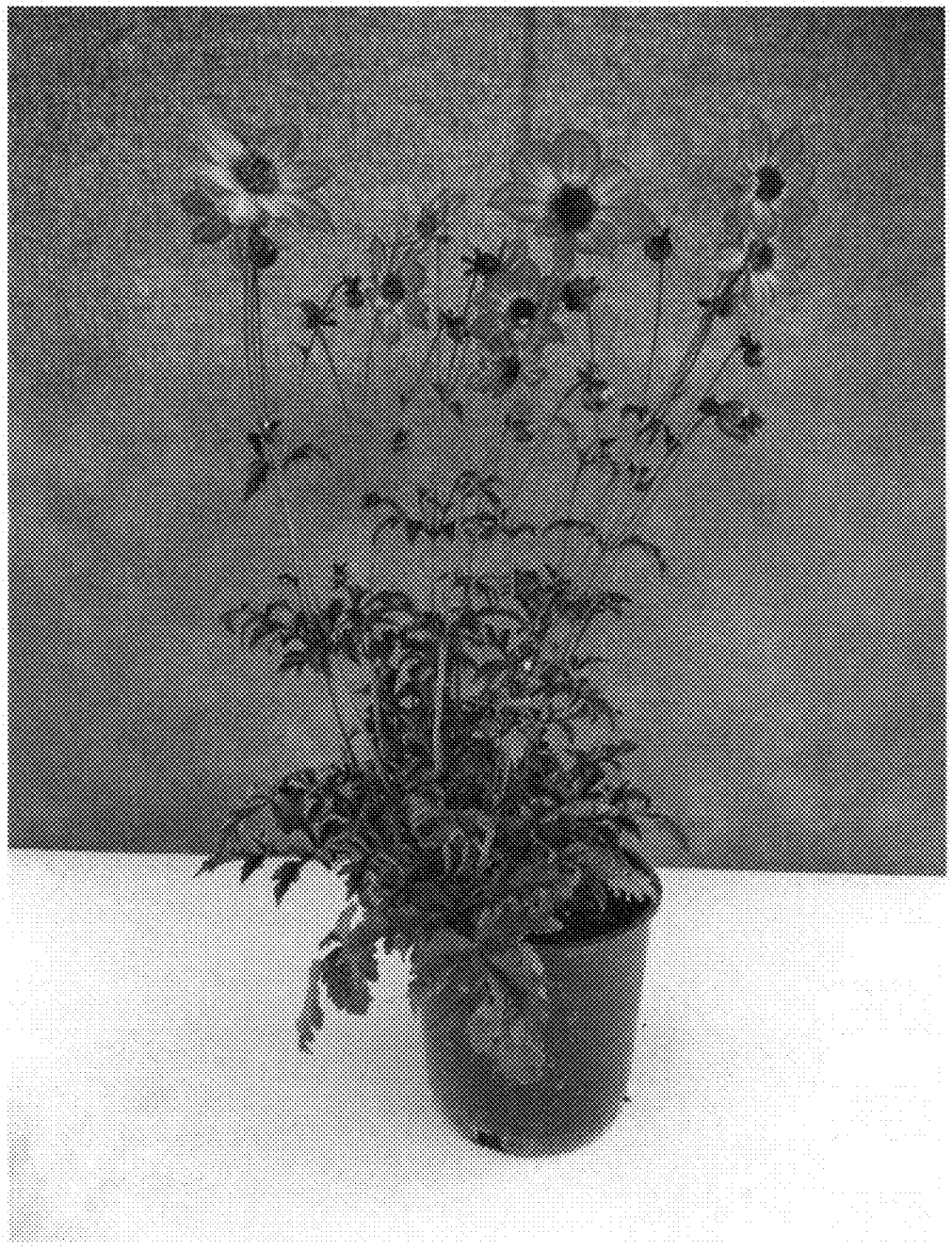

* * * * *